(12) United States Patent
Scheurle et al.

(10) Patent No.: US 11,407,635 B2
(45) Date of Patent: Aug. 9, 2022

(54) BONDING PAD LAYER SYSTEM, GAS SENSOR AND METHOD FOR MANUFACTURING A GAS SENSOR

(71) Applicant: Robert Bosch GmbH, Stuttgart (DE)

(72) Inventors: Andreas Scheurle, Leonberg (DE); Bernd Klein, Reutlingen (DE); Heinz Nedelmann, Tuebingen (DE); Heribert Weber, Nuertingen (DE); Isolde Simon, Kusterdingen (DE); Martin Lapisa, Metzingen (DE); Melissa Delheusy, Filderstadt (DE); Michael Knauss, Pfullingen (DE); Raschid Baraki, Reutlingen (DE); Vitaliy Kondrashov, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 438 days.

(21) Appl. No.: 16/625,185

(22) PCT Filed: Jun. 14, 2018

(86) PCT No.: PCT/EP2018/065780
§ 371 (c)(1),
(2) Date: Dec. 20, 2019

(87) PCT Pub. No.: WO2018/234144
PCT Pub. Date: Dec. 27, 2018

(65) Prior Publication Data
US 2020/0140261 A1    May 7, 2020

(30) Foreign Application Priority Data
Jun. 23, 2017 (DE) .......................... 102017210585.2

(51) Int. Cl.
*B81B 7/00* (2006.01)
*B81C 1/00* (2006.01)
(Continued)

(52) U.S. Cl.
CPC ........ *B81B 7/0006* (2013.01); *B81C 1/00095* (2013.01); *G01N 27/221* (2013.01);
(Continued)

(58) Field of Classification Search
CPC .............................. H01L 24/03; B81B 7/0006
See application file for complete search history.

(56) References Cited

U.S. PATENT DOCUMENTS 6,720,243 B2 * 4/2004 Weng ...................... H01L 24/11
438/615
6,762,122 B2 * 7/2004 Mis ......................... H05K 3/244
257/E23.079
(Continued)

FOREIGN PATENT DOCUMENTS

DE    19824400 A1    12/1999
DE    10347416 A1    3/2005
(Continued)

OTHER PUBLICATIONS

International Search Report for PCT/EP2018/065780, dated Sep. 28, 2018.

*Primary Examiner* — William A Harriston
(74) *Attorney, Agent, or Firm* — Norton Rose Fulbright US LLP; Gerard Messina

(57) ABSTRACT

A bonding pad layer system is deposited on a semiconductor chip as a base, for example, a micromechanical semiconductor chip, in which at least one self-supporting dielectric membrane made up of dielectric layers, a platinum conductor track and a heater made of platinum is integrated. In the process, the deposition of a tantalum layer takes place first, upon that the deposition of a first platinum layer, upon that the deposition of a tantalum nitride layer, upon that the deposition of a second platinum layer and upon that the deposition of a gold layer, at least one bonding pad for connecting with a bonding wire being formed in the gold
(Continued)

layer. The bonding pad is situated in the area of the contact hole on the semiconductor chip, in which a platinum conductor track leading to the heater is connected using a ring contact and/or is connected outside this area.

13 Claims, 3 Drawing Sheets

(51) Int. Cl.
*G01N 27/22* (2006.01)
*G01N 33/00* (2006.01)
*H01L 23/00* (2006.01)

(52) U.S. Cl.
CPC ......... *G01N 33/0027* (2013.01); *H01L 24/03* (2013.01); *H01L 24/05* (2013.01); *B81B 2201/0214* (2013.01); *B81B 2207/098* (2013.01); *B81C 2201/0132* (2013.01); *B81C 2201/0133* (2013.01); *B81C 2201/0143* (2013.01); *B81C 2201/0181* (2013.01); *G01N 2027/222* (2013.01); *H01L 24/45* (2013.01); *H01L 24/48* (2013.01); *H01L 2224/0345* (2013.01); *H01L 2224/03505* (2013.01); *H01L 2224/03831* (2013.01); *H01L 2224/04042* (2013.01); *H01L 2224/05019* (2013.01); *H01L 2224/05027* (2013.01); *H01L 2224/05084* (2013.01); *H01L 2224/05169* (2013.01); *H01L 2224/05181* (2013.01); *H01L 2224/05564* (2013.01); *H01L 2224/05573* (2013.01); *H01L 2224/05644* (2013.01); *H01L 2224/45144* (2013.01); *H01L 2224/48463* (2013.01); *H01L 2924/04953* (2013.01); *H01L 2924/1461* (2013.01)

(56) References Cited

U.S. PATENT DOCUMENTS

| | | | |
|---|---|---|---|
| 7,700,406 B2 * | 4/2010 | Fee | H01L 24/03 438/106 |
| 10,256,202 B1 * | 4/2019 | Spry | H01L 23/5226 |
| 2002/0086520 A1 * | 7/2002 | Chiang | H01L 24/11 438/630 |
| 2002/0096764 A1 * | 7/2002 | Huang | H01L 24/13 257/737 |
| 2002/0111010 A1 | 8/2002 | Walker et al. | |
| 2002/0132426 A1 * | 9/2002 | Shinohara | H01L 27/11507 438/257 |
| 2003/0107137 A1 * | 6/2003 | Stierman | H01L 24/48 257/763 |
| 2005/0215045 A1 | 9/2005 | Rinne et al. | |
| 2006/0091536 A1 * | 5/2006 | Huang | H01L 24/05 257/734 |
| 2007/0023919 A1 | 2/2007 | Lin et al. | |
| 2013/0134603 A1 | 5/2013 | Lee et al. | |
| 2015/0362451 A1 | 12/2015 | Hunziker et al. | |

FOREIGN PATENT DOCUMENTS

| | | |
|---|---|---|
| DE | 102015209267 A1 | 11/2016 |
| EP | 0859231 A1 | 8/1998 |

* cited by examiner

BONDING PAD LAYER SYSTEM, GAS SENSOR AND METHOD FOR MANUFACTURING A GAS SENSOR

FIELD

The present invention relates to a bonding pad layer system, a gas sensor and a method for manufacturing a gas sensor.

BACKGROUND INFORMATION

Although applicable to arbitrary micromechanical components, the present invention and the problem underlying it are explained with reference to components having gas sensor chips.

During the manufacture of micromechanical gas sensors, a paste dot which, for example changes its resistance if certain gases are in its proximity, is generally deposited on the electrodes after completion of a micromechanical chip, which has a self-supporting dielectric membrane, in which a heating structure made of platinum and on which interdigital electrode structures are situated, as described for example in European Patent No. EP 085 92 31 A1.

The paste dot, once it is deposited, must be sintered in order to be able to remove organic paste components and to adjust the desired gas sensitivity. Sintering takes place generally at temperatures that may be significantly above 400° C., as described for example, in German Patent Application No. DE 10 2015 209 267 A1. Since the micromechanical substructure/sensor chip is already fully processed during sintering of the paste, the substructure must be able to withstand the sintering process with no functional impairment. This also means that the bonding pads and the bonding pad connections to conductor track levels must not degrade during the sintering process.

There are already micromechanically manufactured gas sensors on the market, in which a gold bonding wire is bonded onto the platinum layer of a tantalum/platinum bonding pad layer system. However, this system lacks sufficient process stability and has, for example, widely scattering bonding wire adhesion values.

It would be advantageous to design a system in which the bonding ability (bonding wire adhesion) has sufficient process stability in order to be able to ensure high-volume manufacturing.

When implementing such a layer system, the conductor track contacting method described in German Patent Application No. DE 198 24 400 A1 for a micromechanical air mass sensor chip is also to be used in order to become independent of potential conductor track breaks due to edge disintegration on contact hole edges. The air mass sensor chip, like the gas sensor chip, also has a self-supporting dielectric membrane, in which a heating structure made of platinum is integrated. In the conductor track contacting method described in German Patent Application No. DE 198 24 400 A1, an aluminum bonding pad is deposited largely in a contact hole and the electrical connection of the platinum conductor track leading to the heater is implemented with the aid of a ring contact inside the contact hole. The aluminum bonding pad is thus deposited inside this contact hole in part on a platinum layer as well as on a layer of the dielectric layer system situated below the platinum layer. This type of contacting ensures that edge disintegration on contact hole edges is unable to result in an interruption of the electrical contacting of the platinum heater structure due to negative etch edges.

SUMMARY

The present invention provides a bonding pad layer system, a gas sensor, and a method for manufacturing a gas sensor.

According to a first aspect, the present invention accordingly relates to a bonding pad layer system situated on a semiconductor chip. This semiconductor chip may, for example, be a micromechanical semiconductor chip, in which at least one self-supporting dielectric membrane with a heater made of platinum is integrated. During the manufacture of the bonding pad layer system, the deposition of a tantalum layer initially takes place, followed by the deposition of a first platinum layer, followed by the deposition of a tantalum nitride layer, followed by the deposition of a second platinum layer and followed by the deposition of a gold layer, which is used for implementing a bonding pad. The gold bonding pad may be connected to a bonding wire, the entire bonding pad layer system being able to be situated on a semiconductor chip, essentially in the area of the contact hole, in which the connection of a platinum conductor track leading to the heater is made with the aid of a ring contact. It is further possible that bonding pads, made up of the aforementioned bonding pad layer system are also situated outside a contact hole area on the semiconductor chip surface and are used for electrically contacting electrode structures.

According to a second aspect, the present invention relates to a gas sensor that includes at least a bonding pad layer system according to the first aspect, as well as a paste dot.

According to a third aspect, the present invention relates to a method for manufacturing a gas sensor that includes a bonding pad layer system and a paste dot, including the steps in the order: providing a semiconductor chip as a base, for example, a micromechanical semiconductor chip, in which at least one self-supporting dielectric membrane with a heater made of platinum is integrated, depositing a tantalum layer, depositing a first platinum layer, depositing a tantalum nitride layer, depositing a second platinum layer, depositing a gold layer, designing at least one bonding pad for connecting to a bonding wire on the gold layer, designing electrode structures, designing a paste dot and sintering the paste dot.

Advantageous refinements of the present invention are described herein.

The present invention provides a bonding pad layer system, a gas sensor and a corresponding manufacturing method, including a specific layer sequence, which is high-temperature stable and, after sintering of the paste dot in a back-end process, makes reliable, stable and high volume capacity wire bonding connections possible. "High-temperature-stable" is understood, in particular, to mean that the bonding pad layer system as well as the functionality of the gas sensor, remain stable with respect to their properties, even when they are exposed to temperatures at which paste dots used for manufacturing gas sensors are sintered. These are, in particular, temperatures in the range of 400° C. and above.

Thus, the present invention allows for the production of a high-temperature-stable bonding pad layer system, as it may be used, for example, for gas sensors in high volume manufacturing.

According to one preferred refinement of the present invention, the semiconductor chip is a micromechanical semiconductor chip, in which at least one self-supporting dielectric membrane that includes dielectric layers, a platinum conductor track and a heater made of platinum are integrated. This allows for a variety of potential applications of the layer system.

According to one preferred refinement of the present invention, at least a bonding pad is situated essentially in the area of a contact hole on the semiconductor chip, in which the connection to a platinum conductor track leading to the heater takes place with the aid of a ring contact.

According to one preferred refinement of the present invention, at least a bonding pad is situated essentially in the area outside the contact hole on the semiconductor chip. Via the bonding pad, a connection may take place to the heater and/or to additional electrode structures and conductor tracks.

As mentioned, the high-temperature stable bonding pad layer system has the layer sequence tantalum/platinum 1/tantalum nitride/platinum 2/gold. According to one preferred refinement of the present invention, the layer thickness of the tantalum layer is 2 to 200 nanometers, the layer thickness of the first platinum layer is 50 to 1000 nanometers, the layer thickness of the tantalum nitride layer is 2 to 200 nanometers, the layer thickness of the second platinum layer is 2 to 400 nanometers and the layer thickness of the gold layer is 50 to 1000 nanometers. The layer thicknesses may thus be optimally adapted to the sintering process in order, for example, to prevent undesirable diffusion processes or to ensure particular functions.

According to one preferred refinement of the present invention, the layer thickness of the tantalum layer is 5 to 50 nanometers, the layer thickness of the first platinum layer is 100 to 500 nanometers, the layer thickness of the tantalum nitride layer is 5 to 50 nanometers, the layer thickness of the second platinum layer is 10 to 150 nanometers and the layer thickness of the gold layer is 200 to 600 nanometers. With an optimum adaptation of the layer thicknesses to the desired function or to the applied sintering process, it is possible to achieve shorter process times during the deposition and lower material consumption.

According to one preferred refinement of the present invention, the layer composition of the tantalum nitride layer is made up of tantalum (Ta) and nitrogen ($N_2$) in the ratio $Ta_xN_y$, x being between 1 and 5 and y being between 0.04 and 6. With the selected layer composition, it is possible to influence or prevent the diffusion behavior of atoms through the tantalum nitride layer.

According to one preferred refinement of the present invention, the layer composition of the tantalum nitride layer is stoichiometric. As a result, it is possible to control the diffusion of atoms of other layers through the tantalum nitride layer during the sintering process.

According to one preferred refinement of the present invention, the tantalum layer and the first platinum layer of the bonding pad layer system are also used for manufacturing electrical conductor tracks and electrodes, for example, in the form of interdigital structures. Thus, it is possible to provide precise micro-electrical components having low power consumption in a minimum amount of space.

According to one preferred refinement of the present invention, at least one bonding pad is designed for connecting to a bonding wire outside the contact hole area on the first platinum layer of the bonding pad layer system. In this way, it is possible with the aid of a bonding wire to safely and with long-term stability, electrically contact the conductor tracks made up of the tantalum layer and the first platinum layer of the bonding pad layer system leading to the electrode structures. Whereas tantalum nitride layers are normally manufactured with the aid of reactive sputter technology, the tantalum nitride layers according to one preferred refinement of the method according to the present invention may also be formed by tempering applied tantalum layers at temperatures above 600° C. in an ammonia ($NH_3$)/hydrogen ($H_2$) atmosphere or in a nitrogen ($N_2$)/hydrogen ($H_2$) atmosphere. This allows for a particularly exact adjustment of the composition of the tantalum nitride layer.

According to one preferred refinement of the method according to the present invention, the tantalum and the first platinum layer are formed with the aid of a photoresist mask and of a subsequent etching step as conductor tracks and electrode structures, for example, as interdigital structures, making it possible for the etching to take place with the aid of IBE etching, plasma etching, wet chemical etching and combinations thereof.

BRIEF DESCRIPTION OF THE DRAWINGS

The present invention is explained in greater detail below with reference to the exemplary embodiments shown in the schematic figures.

DETAILED DESCRIPTION OF EXAMPLE EMBODIMENTS

Figure 1:
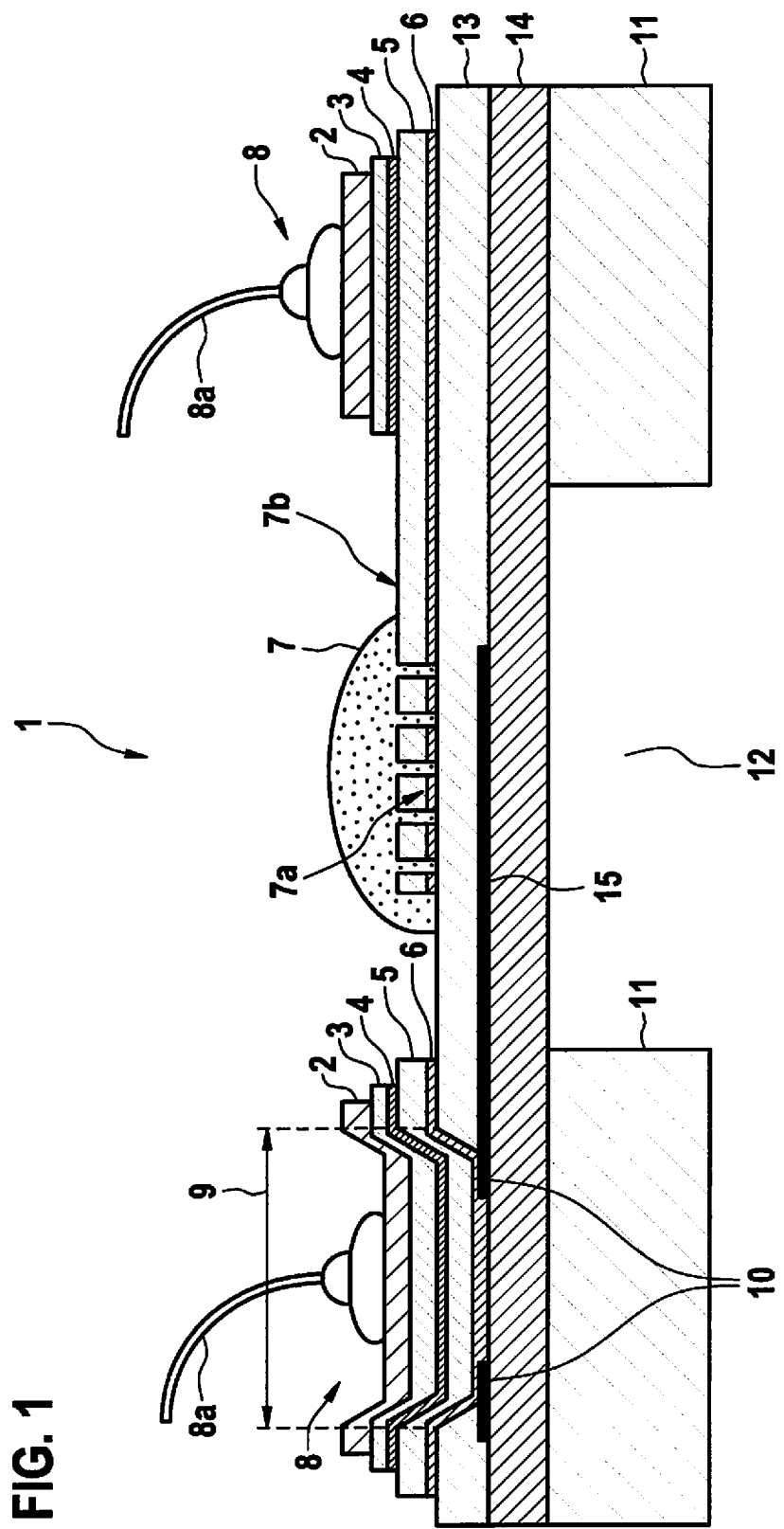
FIG. 1 schematically shows a representation of a gas sensor according to a first specific embodiment of the present invention.

Identical reference numerals in the figures refer to identical or functionally identical elements.

FIG. 1 is a schematic representation of a gas sensor according to a first specific embodiment of the present invention.

One possible implementation of a gas sensor according to the present invention is shown, including a bonding path layer system 1, including a micromechanical semiconductor chip 11 having a cavern 12 as a base, two dielectric layers 13 and 14, a platinum conductor track 10 to heater 15 in cavern area 12, a tantalum layer 6, upon which a first platinum layer 5 is deposited, upon that a tantalum nitride layer 4 is deposited, upon that a second platinum layer 3 is deposited, upon that a gold layer 2 is deposited, the individual layers being deposited over the entire area, even over a contact hole 9 and the individual layers subsequently being structured with the aid of standard methods. A bonding pad 8, a bonding wire 8a, a paste dot 7 and schematically an electrode structure (for example, an interdigital structure) 7a as well as a conductor track 7b are also depicted. Bonding pad 8 may be designed essentially in the area of a contact hole 9, in particular, directly above the contact hole or also outside contact hole 9.

Dielectric membrane layers 13 and 14 may include silicon dioxide ($SiO_2$), silicon nitride ($Si_3N_4$) and mixtures thereof and each separately may be made of multiple dielectric layers or different dielectric layer sequences.

The core of the present invention is to implement a bonding pad 8, in which a bonding wire 8a made of gold may be reliably fastened to a gold layer 2 following a sintering process. Wire bonding of gold wires to gold bonding pads is normally applied when electrically connecting integrated semiconductor chips. After manufacturing, however, the bonding pads are no longer exposed to temperatures above 400° C. Since gold may increasingly diffuse into platinum and tantalum at high temperatures and under certain atmospheric conditions, and the adhesion of bonding pad 8 to the substructure may deteriorate, according to the present invention, a tantalum nitride layer 4 is also inserted as a diffusion barrier between gold layer 2 and underlying first platinum layer 5 ("platinum 1") and tantalum layer 6, as shown in FIG. 1. Due to the moderate adhesion of gold on tantalum nitride, a second platinum layer 3 ("platinum 2") is also inserted as an adhesive layer between gold layer 2 and tantalum nitride layer 4 acting as a diffusion barrier. The result, therefore, based on the foregoing, is a bonding pad layer system, which is composed of the following: tantalum/platinum 1/tantalum nitride/platinum 2/gold. This bonding pad layer system is situated, starting with tantalum 6 as the first layer deposition, on a semiconductor chip 11, including a cavity 12, dielectric layers 13 and 14 and platinum conductor track 10 or in a contact hole 9 present therein.

Parts of this layer system 1 may also be used during the manufacture of a gas sensor for manufacturing electrodes 7a. Thus, for example, tantalum layer 6 and first platinum layer 5 may be designed via the targeted use of etching masks and etching processes as electrodes 7a and conductor tracks 7b in the membrane area as well as outside the membrane area, on which a paste dot 7 may then be subsequently deposited. Situated in the bonding pad area outside the membrane is then also tantalum nitride layer 4, second platinum layer 3 and gold layer 2 on first platinum layer 5 and tantalum layer 6, which results in the bonding pad layer system tantalum/platinum 1/tantalum nitride/platinum 2/gold layer already described above.

When adopting the structure of a semiconductor chip, for example, that of a micromechanical air mass sensor from the related art, it is possible to manufacture the base for a gas sensor chip using adapted masks. Since aluminum and platinum react with one another already at relatively low temperatures (200 to 300° C.), which may result in, among other things, the formation of holes in the contact area of both materials, and in addition, bonding pads 8 in a gas sensor are unable to be separately protected, for example, via gelling, from environmental influences, there is the need to substitute the chemically unstable aluminum for chemically stable materials such as, for example, gold or platinum.

Described bonding pad layer system 1 therefore utilizes platinum and gold as components of a new, high-temperature stable bonding pad layer system 1. To be able to ensure a solid adhesion of first platinum layer 5 of the layer system on a layer of dielectric layers 13 and 14 of the semiconductor chip, a tantalum layer 6 is initially deposited on the semiconductor chip. This layer contacts (ring contact) platinum conductor track lead 10 of heater 15 made of platinum in contact hole 9 and also serves as an adhesive layer for the subsequent layers on dielectric layers 13 and 14. Tantalum nitride layer 4, second platinum layer 3 and gold layer 2 are subsequently deposited on this tantalum layer 6 and first platinum layer 5 and the entire layer system is structured. The individual layers are deposited with the aid of sputtering, reactive sputtering, chemical vapor deposition (CVD), physical vapor deposition (PVD), pulsed laser re-deposition and/or atomic layer deposition (ALD). With the selection of suitable deposition processes, it is possible to optimize process costs and process times.

With suitable process management and correspondingly adapted masks, it is further possible to structure the deposited layers in such a way that electrode structures (for example, interdigital structures) 7a and conductor tracks 7b are produced, which are made up of a sequence of first platinum layer 5 and tantalum layer 6. Generally, the procedure in this case is that gold layer 2, second platinum layer 3 and tantalum nitride layer 4 are structured with the aid of a first mask layer and first platinum layer 5 and tantalum layer 6 are subsequently structured with the aid of a second mask layer. Whereas bonding pad structures are produced using the first mask layer, which are later used for, among other things, electrically contacting electrodes 7a, the second mask layer is used for manufacturing electrodes 7a, their electrical lines, as well as for implementing final bonding pad 8 in the area of contact hole 9 and of final bonding pad 8 outside contact hole area 9. In this way, the layer sequence of first platinum layer 5 and of tantalum layer 6, which is a component of described bonding pad layer system 1 according to the present invention, may be utilized at the same time for manufacturing electrodes 7a and electrical conductor tracks 7b on a semiconductor chip, which functions as a sensor chip.

The individual layers may be structured with the aid of masks and standard etching methods, such as IBE etching, plasma etching, wet chemical etching, or combinations thereof. A wet chemical etching step may be used, for example, to separate the edges of gold layer 2 from the edges of second platinum layer 3 and of tantalum nitride layer 4. In this way, it may be ensured that gold is unable to diffuse over edges of second platinum layer 3 and of tantalum nitride layer 4 and pass uncontrolled into first platinum layer 5 or into tantalum layer 6. The layer thicknesses and layer compositions of the individual layers may also be adapted to the sintering conditions (temperature, atmosphere, time).

Thus, it is possible, for example, to extend the diffusion paths by increasing layer thicknesses. This means, the atoms of one material need longer in order to diffuse through another material. Since the inter-diffusion of materials is a function of temperature and/or time, the increase of a layer thickness may allow for a sintering process that is capable of proceeding at a higher temperature and/or for a longer time.

Typical layer thicknesses in this case are in the range of a few nanometers to as many as multiple micrometers. Preferred layer thicknesses are in the range of 2 to 200 nanometers for tantalum layer 6, in the range of 50 to 1000 nanometers for first platinum layer 5, in the range of 2 to 200 nanometers for tantalum nitride layer 4, in the range of 2 to 400 nanometers for second platinum layer 3 and in the range of 50 to 1000 nanometers for gold layer 2. Particularly preferred layer thicknesses are in the range of 5 to 50 nanometers for tantalum layer 6, in the range of 100 to 500 nanometers for first platinum layer 5, in the range of 5 to 50 nanometers for tantalum nitride layer 4, in the range of 10 to 150 nanometers for second platinum layer 3 and in the range of 200 to 600 nanometers for gold layer 2.

Essentially two aspects must be considered when selecting the layer thickness. First are the necessary sintering conditions (temperature, atmosphere, time) and the process costs required for manufacturing the layer. The possibility of using smaller layer thicknesses means shorter processing times during the deposition, less material consumption, as well as shorter processing times during the structuring of the layer. Since these three points result in lower process costs, the effort is made to select the optimum layer thicknesses for the respective sintering conditions with respect to costs and function. In the case of tantalum nitride layer 4, the layer composition is also a factor, which has an influence on the diffusion behavior of atoms through the layer. It may therefore be advantageous to vary the layer composition of tantalum nitride layer 4 as a function of the sintering conditions. The variations in such case may be in the following range: $Ta_xN_y$, with x being from 1 to 5 and y being from 0.04 to 6. However, a stoichiometric composition of tantalum nitride layer 4 is preferably sought. As previously described above, tantalum nitride layer 4 may be manufactured, for example, via sputtering. It is furthermore also possible, however, to be able to manufacture tantalum nitride layer 4 by tempering Ta layers at temperatures above 600° C. in an ammonia ($NH_3$)/hydrogen ($H_2$) atmosphere or in a nitrogen ($N_2$)/hydrogen ($H_2$) atmosphere.

Figure 2:
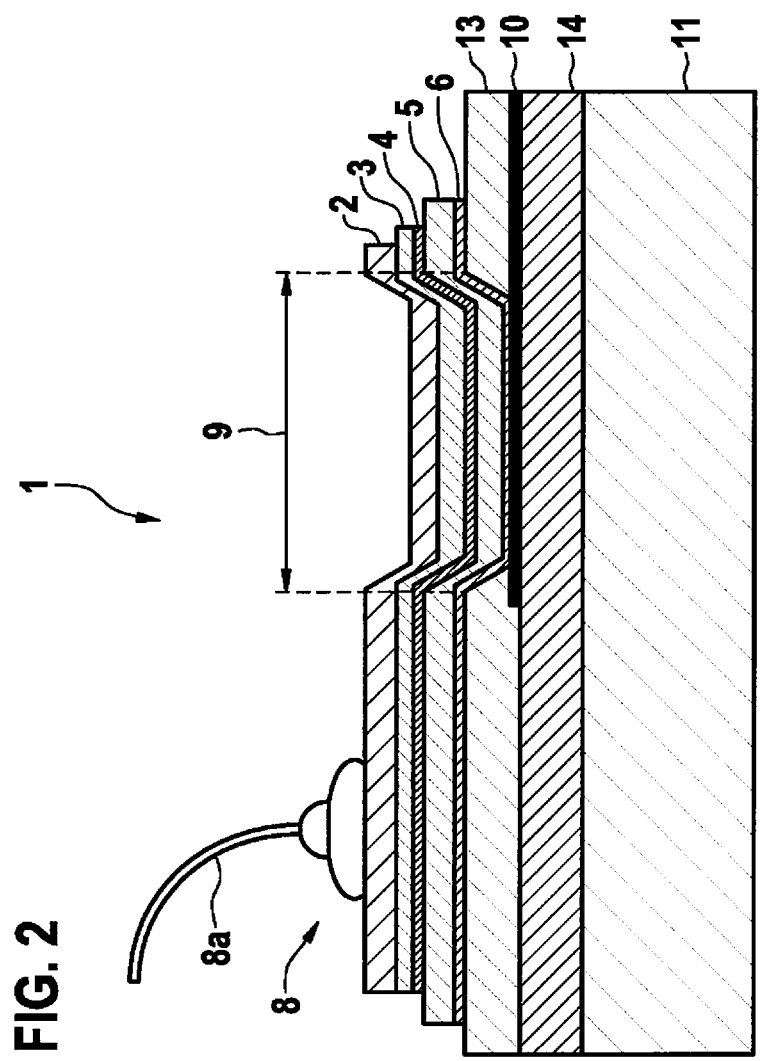
FIG. 2 schematically shows a representation of a bonding pad layer system according to a second specific embodiment of the present invention.

FIG. 2 is a schematic representation of a bonding pad layer system according to a second specific embodiment of the present invention.

One possible implementation of a bonding pad layer system 1 according to the present invention is shown, including a micromechanical semiconductor chip 11 as a base, two dielectric layers 13 and 14, a platinum conductor track 10 of heater 15, a tantalum layer 6, upon which a first platinum layer 5 is deposited, upon that a tantalum nitride layer 4 is deposited, upon that a second platinum layer 3 is deposited, upon that a gold layer 2 is deposited. In contrast to the first specific embodiment, a bonding wire 8*a* and a bonding pad 8 are formed in this case outside of contact hole 9.

As depicted in FIG. 2, it is also possible to design a classic contact hole 9, in which to contact hole platinum conductor track lead 10 to heater 15 with provided bonding pad layer system 1 and to provide a bonding wire 8*a* and a bonding pad 8 outside contact hole 9 on bonding pad layer system 1.

Figure 3:
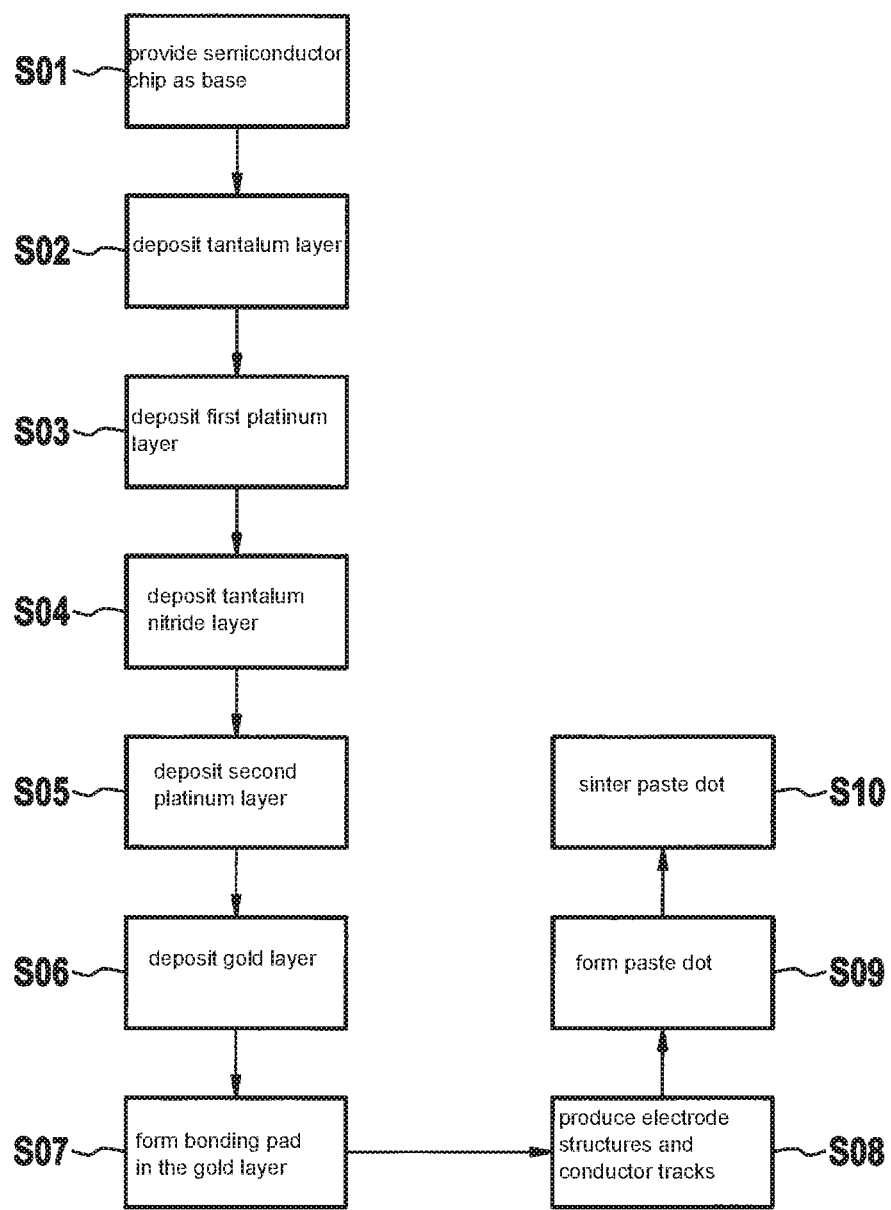
FIG. 3 schematically shows a flow chart for explaining a method for manufacturing a bonding pad layer system or a gas sensor according to another specific embodiment.

FIG. 3 schematically shows a flow chart for explaining a method for manufacturing a bonding pad layer system or a gas sensor according to another specific embodiment. The method according to FIG. 3 is suitable for manufacturing the devices described above and may be modified according to all variants and refinements described with respect to these devices and vice versa.

A semiconductor chip is provided in a step S01 as a base, for example, a micromechanical semiconductor chip 11, in which at least one self-supporting dielectric membrane made of dielectric layers 13, 14, of platinum conductor track 10 and of a heater 15 made of platinum is integrated. A tantalum layer 6 is deposited in a step S02. A first platinum layer 5 is deposited in a step S03. A tantalum nitride layer 4 is deposited in a step S04. A second platinum layer 3 is deposited in a step S05. A gold layer 2 is deposited in a step S06. A bonding pad 8 is formed in a step S07 in gold layer 2 for connecting to a bonding wire 8*a*, essentially in the area of a contact hole 9 on semiconductor chip 11, in which platinum conductor track 10 leading to heater 15 is connected with the aid of a ring contact. It is also possible in this step to provide bonding pads outside contact hole area 9. Electrode structures 7*a* and conductor tracks 7*b* are produced in a step S08. A paste dot 7 is formed in a step S09. Paste dot 7 is sintered in a step S10. Steps S01 through S10 are preferably carried out preferably in the order of their numbering. A bonding wire 8*a* may be attached to bonding pad 8.

Although the present invention has been described with reference to preferred exemplary embodiments, it is not limited thereto. The materials and topologies cited are, in particular, only exemplary and not limited to the examples discussed.

Particularly preferred, additional applications for the bonding pad layer system according to the present invention are, for example, gas sensors, which are used in exhaust sensors, for example, in the automotive industry or the like.

What is claimed is:

1. A bonding pad layer system, comprising:
a semiconductor chip as a base, upon which a tantalum layer, a first platinum layer, a tantalum nitride layer, a second platinum layer, and a gold layer, are sequentially deposited, at least one bonding pad being formed in the gold layer for connecting to a bonding wire.

2. The bonding pad layer system as recited in claim 1, wherein the semiconductor chip is a micromechanical semiconductor chip, in which at least one self-supporting dielectric membrane including dielectric layers, a platinum conductor track and a heater made of platinum is integrated.

3. The bonding pad layer system as recited in claim 2, wherein at least one of the at least one bonding pad is situated in an area of a contact hole on the semiconductor chip, in which a platinum conductor track leading to the heater is electrically connected with using a ring contact.

4. The bonding pad layer system as recited in claim 1, wherein at least one of the at least one bonding pad is situated in an area outside the contact hole on the semiconductor chip.

5. A bonding pad layer system as recited in claim 1, wherein:
a layer thickness of the tantalum layer is 2 to 200 nanometers,
a layer thickness of the first platinum layer is 50 to 1000 nanometers,
a layer thickness of the tantalum nitride layer is 2 to 200 nanometers,
a layer thickness of the second platinum layer is 2 to 400 nanometers, and
a layer thickness of the gold layer is 50 to 1000 nanometers.

6. The bonding pad layer system as recited in claim 1, wherein
a layer thickness of the tantalum layer is 5 to 50 nanometers,
a layer thickness of the first platinum layer is 100 to 500 nanometers,
a layer thickness of the tantalum nitride layer is 5 to 50 nanometers,
a layer thickness of the second platinum layer is 10 to 150 nanometers, and
a layer thickness of the gold layer is 200 to 600 nanometers.

7. The bonding pad layer system as recited in claim 1, wherein a layer composition of the tantalum nitride layer is made up of tantalum (Ta) and nitrogen (N) in the ratio $Ta_xN_y$, x being between 1 and 5 and y being capable of varying between 0.04 and 6.

8. The bonding pad layer system as recited in claim 1, wherein a layer composition of the tantalum nitride layer is stoichiometric.

9. The bonding pad layer system as recited in claim 1, wherein the tantalum layer and the first platinum layer are electrical electrodes and conducting tracks).

10. The boding pad layer system as recited in claim 2, wherein the micromechanical semiconductor chip is a gas sensor.

11. A method for manufacturing a gas sensor including a bonding pad layer system and a paste dot, comprising the following steps in the order:
- a) providing a micromechanical semiconductor chip as a base, in which at least one self-supporting dielectric membrane made up of dielectric layers and a platinum conductor track for electrically contacting a heater made of platinum is integrated;
- b) depositing a tantalum layer;
- c) depositing a first platinum layer;
- d) depositing a tantalum nitride layer;
- e) depositing a second platinum layer;
- f) depositing a gold layer;
- g) providing at least one bonding pad for connecting to a bonding wire on the gold layer in an area of a contact hole on the semiconductor chip, in which a platinum conductor track leading to the heater is connected using a ring contact, and providing at least one bonding pad outside a contact hole, which is used to electrically contact electrode structures and conductor tracks;
- h) providing the electrode structures and the conductor tracks;
- i) providing a paste dot; and
- j) sintering the paste dot.

12. The method as recited in claim 11, wherein the tantalum nitride layer is formed by tempering tantalum layers at temperatures above 600° C. in an ammonia/hydrogen atmosphere or in a nitrogen/hydrogen atmosphere.

13. The method as recited in claim 11, wherein the tantalum layer and the first platinum layer are etched to form the electrode structures and conductor tracks, the etching capable of taking place using IBE etching and/or plasma etching and/or wet chemical etching.

* * * * *